United States Patent [19]

Kaneshiki et al.

[11] Patent Number: 4,873,383

[45] Date of Patent: Oct. 10, 1989

[54] METHOD FOR SELECTIVE ISOLATION OF DICHLOROBENZENE

[75] Inventors: Toshitaka Kaneshiki; Osamu Narukawa; Tadayoshi Haneda; Toshiyuki Endo, all of Koriyama, Japan

[73] Assignee: Hodogaya Chemical Co., Ltd., Tokyo, Japan

[21] Appl. No.: 150,400

[22] Filed: Jan. 29, 1988

[30] Foreign Application Priority Data

Feb. 10, 1987 [JP] Japan .................................. 62-27169

[51] Int. Cl.$^4$ ............................................. C07C 17/38
[52] U.S. Cl. ...................................... 570/211; 570/190
[58] Field of Search ................................. 570/190, 211

[56] References Cited

U.S. PATENT DOCUMENTS 4,244,062 3/1981 Wambach et al. ................... 570/211
4,695,667 9/1987 Sumitani et al. ..................... 585/481

FOREIGN PATENT DOCUMENTS 0199212 10/1986 European Pat. Off. ............ 570/211
246673 11/1987 European Pat. Off. ............ 570/211
0249883 12/1987 European Pat. Off. ............ 570/211
3327146 6/1984 Fed. Rep. of Germany ...... 570/211
13727 1/1985 Japan .................................. 570/211
1268636 11/1986 Japan .................................. 570/211
902724 8/1962 United Kingdom .
2166734 5/1986 United Kingdom ................ 570/211

Primary Examiner—Warren B. Lone
Attorney, Agent, or Firm—McAulay Fisher Nissen & Goldberg

[57] ABSTRACT

A selective isolation of m-dichlorobenzene is carried out at a high efficiency by bringing an isomeric mixture containing m- and o- and/or p-dichlorobenzenes into contact with an absorbing material comprising a TPZ-3 type zeolite consisting of at least one aluminosilicate compound of the formula (I):

$$M_{2/\underline{n}}O \cdot Al_2O_3 \cdot \underline{x}SiO_2 \cdot \underline{m}H_2O \qquad (I)$$

wherein M = a mono or di-valent cation, for example, H$^+$, Li$^+$ or Na$^+$, $\underline{n}$=1 or 2, $\underline{x}$=10 or more, and $\underline{m}$=0 or 1 or more, to selectively absorb dichlorobenzene by the absorbing material, and then, by collecting the non-absorbed fraction of the isomeric mixture.

16 Claims, 1 Drawing Sheet

METHOD FOR SELECTIVE ISOLATION OF DICHLOROBENZENE

BACKGROUND OF THE INVENTION

1. Field of the Invention

The present invention relates to a method for a selective isolation of m-dichlorobenzene from an isomeric mixture thereof. More particularly, the present invention relates to a method for selectively isolating m-dichlorobenzene, which is useful as an intermediate of pesticides (agricultural chemicals), medicines and dyestuffs, from an isomeric mixture thereof by using an absorbing material.

2. Description of the Related Arts

It is known that m-dichlorobenzene can be prepared by the chlorination of benzene or chlorobenzene or by the isomerization of o- and/or p-dichlorobenzene. The resultant product is in the form of an isomeric mixture of m-dichlorobenzene and o- and/or p-dichlorobenzene.

It is also known that o-dichlorobenzene (o-DCB) has a boiling point of 180.4° C., m-dichlorobenzene (m-DCB) has a boiling point of 173.0° C., and p-dichlorobenzene (p-DCB) has a boiling point of 174.1° C.; namely, these materials have boiling points which are close to each other.

In the dichlorobenzene isomers, the o-isomer exhibits a higher melting point than those of m- and p-isomers, and thus can be isolated and collected by a rectification column having a high stage number. However, it is very difficult to completely isolate the o-isomer from the m- and p-isomers by a high stage rectification.

Japanese Unexamined Patent Publication No. 50-19722 discloses a method for separating m- and p-DCB isomers. In this method, the m-isomer is isolated by an extract-distillation in the presence of a natural polar solvent, for example, hexamethylphosphotriamide or dimethylsulfoxide, and then the p-isomer extracted in the natural polar solvent is isolated from the natural polar solvent solution by distillation thereof.

However, the extract distillation method is disadvantageous in that the yield and purity of the isolated m-isomer are unsatisfactory.

In another separating method, the isomeric mixture is subjected to a sulfonation procedure and then m-dichlorobenzene-4-sulfonic acid is isolated from the sulfonation product by crystallization deposition.

This method is disadvantageous in that the purity of the resultant isolated m-isomer is not satisfactorily high and the isolation procedures are costly.

Still other separating methods, in which various faujasite types (X or Y type) of zeolites are used as an absorbing material to isolate the m-DCB isomer as a raffinate or extract fraction from a DCB isomeric mixture, are disclosed in Japanese Examined Patent Publication No. 37-5155 and Japanese Unexamined Patent Publication Nos. 52-62229, 53-105434, 58-131,924, 58-150,524, and 61-268,636.

However, the conventional faujasite type zeolite does not effect a satisfactory isolation of the m-isomer and, therefore, it is practically impossible to obtain a high purity m-isomer. Furthermore, the conventional isolating method in which the faujasite type zeolite is used as an absorbing material is disadvantageous in that the isolation of the m-isomer must be carried out in the presence of an eluent, and the m-isomer must be separated from the eluent by distillation of the eluent m-isomer solution.

Under the above-mentioned circumstances, there is a need for a new m-DCB isomer-isolating method which can be effected at a high efficiency by a simple and easy operation.

SUMMARY OF THE INVENTION

An object of the present invention is to provide a method for the selective isolation of m-dichlorobenzene at a high efficiency.

Another object of the present invention is to provide a method for the selective isolation of m-dichlorobenzene from a dichlorobenzene isomeric mixture by utilizing a specific absorbing material in a simple and easy operation.

The above-mentioned objects are attained by the method of the present invention, which comprises the steps of bringing an isomeric mixture containing m-dichlorobenzene and at least one member selected from o- and p-dichlorobenzenes into contact with an absorbing material comprising a TPZ-3 type zeolite consisting essentially of at least one aluminosilicate compound of the formula (I):

$$M_{2/n}O \cdot Al_2O_3 \cdot xSiO_2 \cdot mH_2O \tag{I}$$

wherein, M represents a member selected from monovalent and divalent cations, $n$ represents an integer of 1 when M represents a monovalent cation, or of 2 when M represents a divalent cation, $x$ represents an integer of 10 or more, and $m$ represents zero or an integer of 1 or more, to cause the o- and/or p-dichlorobenzene in the isomeric mixture to be selectively absorbed by the absorbing material; and collecting the selectively non-absorbed fraction of the isomeric mixture.

DESCRIPTION OF THE PREFERRED EMBODIMENTS

Figure 1:
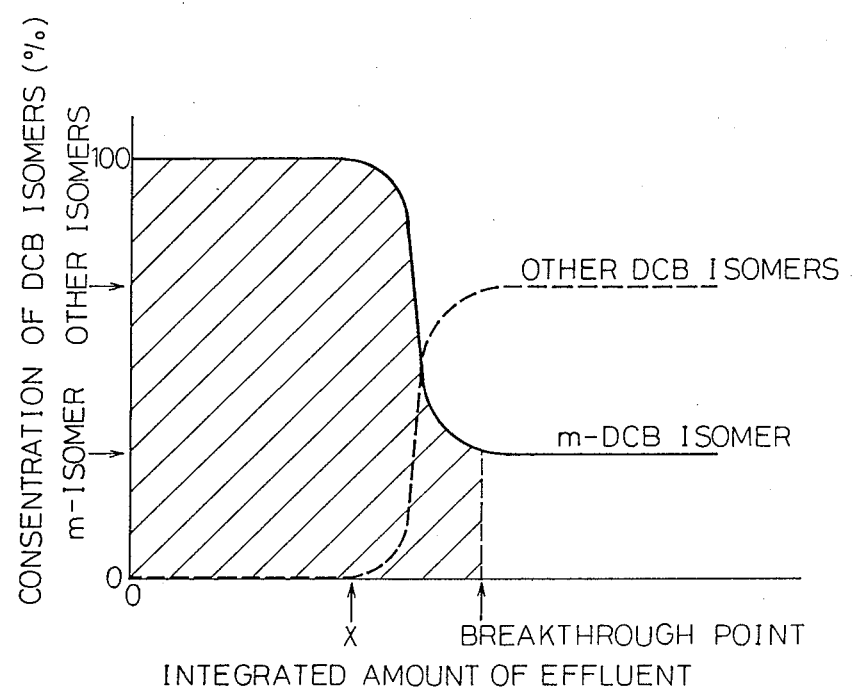
FIG. 1 shows a relationship between the integrated amount of a non-absorbed fraction, that is, effluent, of a dichlorobenzene isomeric mixture and the concentrations of m-dichlorobenzene and other dichlorobenzene isomers in the non-absorbed fraction.

In the process of the present invention, m-dichlorobenzene is selectively isolated from a dichlorobenzene isomeric mixture containing m-dichlorobenzene and o- and/or p-dichlorobenzene by utilizing a specific absorbing material comprising a TPZ-3 type zeolite.

It is well known that the TPZ-3 type zeolite is useful as an isomerization reaction catalyst. Also, it is known that the TPZ-3 type zeolite can be used to separate cyclohexane from n-hexane. However, it is not known that the TPZ-3 type zeolite can be used to selectively isolate m-dichlorobenzene from other dichlorobenzene isomers.

The TPZ-3 type zeolite disclosed in Japanese Unexamined Patent Publication No. 57-95821, is characterized by a high content of silica component, and thus is definitely distinguished from ZSM type zeolites, for example, ZSM-5 type and ZSM-11 type zeolites, and from Zeta-3 type zeolite. Namely, the TPZ-3 type zeolite exhibits a distinctive X-ray diffraction pattern and absorption property in comparison with those of the conventional types of zeolites. Also, the TPZ-3 type zeolite has a number of pores formed therein and has a larger size than that of the above-mentioned conventional zeolites.

The TPZ-3 type zeolite usable for the present invention consists essentially of at least one aluminosilicate compound of the composition formula (I):

$$M_{2/e,uns/n/}O \cdot Al_2O_3 \cdot \underline{x}SiO_2 \cdot \underline{m}H_2O \qquad (I)$$

wherein M represents a monovalent or divalent cation, $\underline{n}$ is an integer of 1 when M is a monovalent cation, or an integer of 2 when M is a divalent cation, for example, $H^+$ or a cation of an alkali metal or alkaline earth metals, $\underline{x}$ is an integer of 10 or more, preferably 30 to 200, and $\underline{m}$ is zero or an integer of 1 or more, preferably, zero.

In the aluminosilicate compound of the formula (I), the monovalent cation represented by M is preferably selected from $H^+$ (proton), $Na^+$ and $Li^+$.

The absorbing material is preferably used in an anhydrous state, i.e., in the formula (I), $\underline{m}$ is zero.

The TPZ-3 type zeolite exhibits a specific selective absorbing property to the dichlorobenzene isomers. That is, the intensity of absorption of the dichlorobenzene isomers to the TPZ-3 type zeolite is in the following order.

$$\text{m-isomer} < < \text{o-isomer} \approx \text{p-isomer}$$

The TPZ-3 type zeolite selectively absorbs the o- and p-isomers at a high absorption intensity but does not absorb the m-isomer. Accordingly, as a result of the absorption procedure of the dichlorobenzene isomeric mixture by the TPZ-3 type zeolite, the m-isomer can be selectively isolated as a non-absorbed fraction or an effluent, at a high yield.

The TPZ-3 type zeolite can be produced from a reaction mixture comprising N,N,N,N',N',N'-hexaalkyl-1,6-hexane diammonium ion-supply material, alkali metal ion-supply material, silica-supply material, aluminasupply material, and water by heating the reaction mixture until the aluminosilicate compound of the formula (I) is produced in the form of a porous crystalline material.

Usually, the aluminosilicate compound of the formula (I) is produced in the form of an Na-TPZ-3 type zeolite of the formula (II):

$$Na_2O \cdot Al_2O_3 \cdot \underline{x}SiO_2O \qquad (II)$$

wherein $\underline{x}$ and $\underline{m}$ are as defined above, and $\underline{x}$ is preferably 30 to 200 and $\underline{m}$ is zero.

In the Na-TPZ-3 type zeolite of the formula (II), the sodium ion ($Na^+$) can be easily replaced by other cations.

The cation exchange of the TPZ-3 type zeolite can be effected by bringing a TPZ-3 type zeolite into contact with a cation exchange liquid consisting of an aqueous solution of a water-soluble nitrate or halide, for example, chloride, of another cation to be exchanged for the cation in the zeolite. The cation exchange procedure can be effected in a single step operation or multiple step operations. Also, the cation exchange procedure can be conducted in a continuous operation or in a batch type operation.

Usually, the cation exchange procedure is carried out at a temperature of from 20° C. to 100° C. However, to promote the cation exchange reaction, preferably the cation exchange temperature is in the range of from 50° C. to 100° C.

After the cation exchange reaction is completed, the resultant zeolite is washed to an extent such that the corresponding anion, for example, $NO_3^-$ or $Cl^-$, can not be detected.

In the process of the present invention, a dichlorobenzene isomeric mixture is brought into contact with an absorbing material comprising the TPZ-3 type zeolite.

The TPZ-3 type zeolite is preferably in an anhydrous form. For this purpose, the TPZ-3 type zeolite is heated at a temperature of 100° C. or more to decrease the content of water of crystallization in the zeolite crystals; preferably at 300° C. to 600° C. to completely eliminate the water of crystallization from the zeolite crystals.

The absorbing material to be used in the method of the present invention is in the form of fine particles (fine powder), grains, pellets, granules, lumps or other shaped articles which may be formed by compression molding or extruder shaping. In the shaping procedure, if necessary, a binder, for example, bentonite or alumina sol, is mixed in a small amount, for example, 30% by weight or less, with the TPZ-3 type zeolite.

Where the selective isolation method of the present invention is carried out on a small scale, the absorbing material may be in the form of a fine powder. However, the fine powder causes a large loss of pressure when the dichlorobenzene isomeric mixture flows through the fine powder, and hinders that flow. Therefore, if the method of the present invention is to be carried out on an industrial or large scale, the absorbing material is preferably in the form of pellets having a size of from 0.1 mm to 10 mm. The shape and size of the pellets are variable depending on the type and scale of the absorbing apparatus.

The absorbing step in the method of the present invention can be carried out in a continuous type operation or a batch type operation. Where the absorbing step is carried out on a small scale, the batch type operation is convenient because the batch type absorbing apparatus is simple and the operation thereof is easy.

Preferably, the absorbing step in the method of the present invention is carried out in an absorbing apparatus provided with one or more absorbing columns, more preferably two or more absorbing columns. Where the absorbing apparatus is provided with two or more absorbing columns, one or more absorbing columns are used for the absorption procedure and the remaining column or columns are used for desorption. Namely, each column is used alternately for the absorption and desorption.

In the absorption procedure, the o- and p-dichlorobenzene isomers are selectively absorbed by the TPZ-3 type zeolite and the selectively non-absorbed fraction consisting essentially of m-dichlorobenzene is collected from the absorption column. After the absorption procedure is completed, a nitrogen gas is introduced into the absorption column, to discharge any remaining non-absorbed isomeric mixture from the absorption column. The o- and p-dichlorobenzene isomers absorbed by the absorbing material are recovered therefrom by desorption, and the desorbed absorbing material is then subjected to the absorption procedure.

The absorption procedure is preferably carried out at a temperature of from room temperature to 350° C., more preferably from 100° C. to 250° C. When the absorption temperature is excessively low, the absorption effect is sometimes unsatisfactory, and an absorption temperature of more than 350° C. sometimes causes an undesirable side reaction, for example, an isomerization reaction of dichlorobenzene.

Also, the absorption procedure is preferably carried out under a pressure of from the ambient atmospheric pressure to about 50 kg/cm$^2$, more preferably about 30 kg/cm$^2$ or less.

The absorption procedure can be carried out in the presence of a foreign material unless the foreign material has an influence on the absorption and desorption of the o- and p-dichlorobenzene isomers. Therefore, the dichlorobenzene isomeric mixture may be diluted by a solvent, which does not affect the absorption and desorption of the o- and p-isomers.

The desorption procedure for the absorbing material can be carried out by any conventional method, but preferably, the desorption is effected by a steam desorption method at a high desorption efficiency. The TPZ-3 type zeolite is very stable under the steam desorption treatment, and this is one reason why the method of the present invention is industrially advantageous.

The absorption property of the TPZ-3 type zeolite for the dichlorobenzene isomeric mixture will be further explained by referring to FIG. 1.

Where a feed consisting of a dichlorobenzene isomeric mixture is brought into contact with the specific absorbing material of the present invention comprising the TPZ-3 type zeolite, the o- and p-dichlorobenzene isomers, referred to as the A component, are selectively absorbed by the absorbing material and the selectively non-absorbed fraction is discharged as an effluent from the absorbing system.

Referring to FIG. 1, in the initial stage of the absorption procedure, that is, until the integrated amount of the effluent reaches X, the effluent consists essentially of m-dichlorobenzene; namely, the concentrations of m-dichlorobenzene and the A component in the non-absorbed fraction are approximately 100% and 0%, respectively.

After the integrated amount of the effluent exceeds X, the absorption activity of the absorbing material falls, and thus the concentration of m-dichlorobenzene in the effluent is reduced and the concentration of the A component in the effluent is increased, as shown in FIG. 1.

When the absorbing activity of the absorption material is completely lost, namely, at or after the breakthrough point, the composition of the effluent is the same as that of the feed, as shown in FIG. 1.

In FIG. 1, the hatched area indicate an integrated amount of the m-isomer selectively isolated by the absorbing material in the stage from the start to the breakthrough point of the absorbing procedure. That is, the hatched area corresponds to a total isolating capacity of the absorbing material for the m-isomer.

The percentage isolating capacity C of the TPZ-3 type zeolite for m-dichlorobenzene is determined in accordance with the following equation.

$$C \text{ (wt \%)} = \frac{A \times B}{D}$$

wherein A represents an integrated amount (in grams) of m-dichlorobenzene discharged from the absorbing system from the start to the breakthrough point of the absorption procedure, B represents an average concentration in % by weight of m-dichlorobenzene in the whole effluent, and D represents an amount in grams of the TPZ-3 type zeolite used in the absorbing system.

The greater the percentage isolating capacity C, the higher the absorbing efficiency of the TPZ-3 type zeolite for m-dichlorobenzene, and the higher the purity of the resultant isolated m-dichlorobenzene.

Also, in the method of the present invention the o- and p-dichlorobenzene isomers are selectively absorbed by the TPZ-3 type zeolite and are recovered at a high purity and high efficiency by desorption.

The TPZ-3 type zeolite can be easily reproduced by a conventional method, for example, the steam desorption method, without operational difficulty and without deterioration of the zeolite, and therefore, can be used over a long period of time with a high durability.

The present invention will be further explained by way of specific examples, which, however, are merely representative and do not restrict the scope of the present invention in any way.

REFERENTIAL EXAMPLE 1

[Preparation of an H-TPZ-3 type zeolite absorbing material (I)]

A gel consisting of 61.6 g of a water glass consisting of 30.88% by weight of SiO$_2$, 16.56% by weight of Na$_2$O, and 44.56% by weight of water, 3.32 g of aluminum sulfate 18 hydrate, 4.56 g of N,N,N,N',N',N'-hexamethyl1,6-hexane diammonium salt, 13.50 g of neutralizing agent consisting of a 98% sulfuric acid, and 200 ml of pure water, was heated at a temperature of 160° C. under a spontaneous pressure for one week in an autoclave while gradually stirring the gel.

The reaction product was washed and dried, and an Na-TPZ-3 type zeolite having a molar ratio of SiO$_2$ to Al$_2$O$_3$ of 80:1 and in the form of a fine powder was obtained.

The Na-TPZ-3 type zeolite was subjected to a cation exchange procedure, in which the zeolite powder was treated five times with an aqueous solution of 10% by weight of ammonium nitrate at a liquor ratio of the aqueous solution to the zeolite powder of 2.0 l/kg at a temperature of 95° C. The resultant product was carefully washed with water, dried at a temperature of 150° C. for 5 hours, and sintered at a temperature of 500° C. for 3 hours. An H-TPZ-3 type zeolite powder was obtained, and this zeolite powder exhibited the same X-ray diffraction pattern as that disclosed in Japanese Unexamined Patent Publication (Kokai) No. 57-95821.

The H-TPZ-3 type zeolite powder in an amount of 70 parts by weight was mixed with 30 parts by weight of bentonite (trademark: Tenryu, made by Kanto Bentonite Mining Co.), 0.2 parts by weight of sodium carboxymethylcellulose (n=500), and 100 parts by weight of water. The mixture was kneaded in a mixing kneader for about one hour, and then was extruded and pelletized by a pelletizer to provide pellets having a diameter of 0.5 mm and a length of about 0.4 mm. The pellets were dried at a temperature of 150° C. for 5 hours, and then sintered at a temperature of 500° C. for 3 hours, and an absorbing material (I) consisting of the H-TPZ-3 type zeolite pellets was obtained.

REFERENTIAL EXAMPLE 2

[Preparation of another H-TPZ-3 type zeolite absorbing material (II)]

An Na-TPZ-3 type zeolite powder was prepared in the same manner as that described in Referential Example 1, except that the molar ratio of SiO$_2$ to Al$_2$O$_3$ was 120:1.

In the same manner as that described in Referential Example 1 the Na-TPZ-3 type zeolite powder was converted to an absorbing material (II) consisting of another H-TPZ-3 type zeolite pellets.

REFERENTIAL EXAMPLE 3

[Preparation of still another H-TPZ-3 type zeolite absorbing material (III)]

The same procedures as those described in Referential Example 1 were carried out except that the molar ratio was $SiO_2/Al_2O_3$ was 40:1, and still another type of H-TPZ-3 type zeolite absorbing material (III) was obtained.

EXAMPLES 1 to 5

In Example 1, a metallic absorption column having an inside diameter of 9.8 mm and a length of 16.3 cm was filled with 8.20 g of the absorbing material (I) produced in Referential Example 1 containing 5.74 g of the H-TPZ-3 type zeolite.

A feed consisting of a dichlorobenzene isomeric mixture containing 30% by weight of m-isomer and 70% by weight of p-isomer was introduced into the absorbing column at a flow rate of 0.1 ml/min, at a temperature of 210° C., and under a nitrogen gas pressure of 2 kg/cm$^2$.

A non-absorbed fraction (effluent) discharged from the absorbing column through an exit thereof was collected, and the composition of the non-absorbed fraction was analyzed by a gas chromatography. It was found that, in the initial stage of the absorption procedure, the concentration of the m-isomer was 100%. With the lapse of the absorption time, the concentration of the m-isomer in the non-absorbed fraction decreased. About 25 minutes after the start of the absorption procedure, the absorption procedure had a breakthrough point at which the composition of the non-absorbed fraction become the same as that of the feed.

The integrated amount of the non-absorbed fraction from the start to the breakthrough point of the absorption procedure was 0.43 g, the average concentration of the m-isomer in the non-absorbed fraction was 80.1% by weight, and the m-isomer isolation capacity of the absorbing material was 6.00% by weight, as shown in Table 1.

Next, in Example 1, a nitrogen gas was made to flow through the absorbing column at the same temperature as that mentioned above under a pressure of 3 kg/cm$^2$ for 30 minutes to completely discharge the remaining isomeric mixture. The discharged isomeric mixture was in an amount of 0.45 g and contained 31.2% by weight of the m-isomer.

A mixture gas consisting of steam (molar partial pressure: 0.33) and nitrogen gas (molar partial pressure: 0.67) was introduced into the absorbing column at a flow rate of 60 ml/min, at the same temperature as mentioned above, and under a pressure of 6 kg/cm$^2$. The p-isomer absorbed in the absorbing material was desorbed and discharged together with water. About 30 minutes after the start of the desorption procedure, the discharge of the p-isomer was completed. The total amount of the desorption product was 0.73 g. The average concentration of the p-isomer in the desorption product was 98.2% by weight.

The second to fifth cycles of the same absorption, washing, and desorption procedures as described above were successively carried out in Examples 2 to 4.

The results are shown in Table 1.

After the fifth procedure cycle in Example 5 was completed, the degree of crystallization of the zeolite was determined by an X-ray diffraction analysis. As a result, it was confirmed that no rupture of the crystalline structure of zeolite had occurred.

TABLE 1

| Example No. | Absorption procedure | | | Desorption procedure | |
|---|---|---|---|---|---|
| | Integrated amount of effluent (g) | Average concentration of m-isomer in effluent (% by wt) | m-isomer isolating capacity (C) (% by wt) | Total amount of desorption product (g) | Concentration of p-isomer (% by wt) |
| 1 | 0.43 | 80.1 | 6.00 | 0.73 | 98.2 |
| 2 | 0.43 | 79.1 | 5.93 | 0.72 | 98.0 |
| 3 | 0.45 | 76.9 | 6.03 | 0.71 | 97.6 |
| 4 | 0.42 | 79.2 | 5.80 | 0.75 | 95.8 |
| 5 | 0.44 | 79.0 | 6.06 | 0.74 | 96.1 |

EXAMPLES 6 AND 7 AND COMPARATIVE EXAMPLE 1

In Example 6, the same procedures as those described in Example 1 were carried out except that the H-TPZ-3 type zeolite absorbing material prepared in Referential Example 2 was used in place of that used in Example 1.

In Example 7, the same procedures as those described in Example 1 were carried out except that the H-TPZ-3 type zeolite absorbing material prepared in Referential Example 3 was used in place of that used in Example 1.

In Comparative Example 1, the same procedures as those described in Example 1 were carried out except that the H-TPZ-3 type zeolite absorbing material was replaced by a comparative absorbing material comprising a conventional H-ZSM-5 type zeolite produced by the procedures disclosed in Example 1 of Japanese Examined Patent Publication (Kokoku) No. 46-10,064 in a molar ratio $SiO_{2pl}/Al_2O_3$ of 25:1, and pelletized in the same manner as that disclosed in Example 1.

The results of the absorption and desorption procedures are shown in Table 2.

TABLE 2

| Example No. | Molar ratio SiO$_2$/Al$_2$O$_3$ of zeolite | Absorption procedure | | | Desorption procedure | |
|---|---|---|---|---|---|---|
| | | Integrated amount of effluent (g) | Average concentration of m-isomer in effluent (% by wt) | m-isomer isolating capacity (C) (% by wt) | Total amount of desorption product (g) | Concentration of p-isomer (% by wt) |
| Example 6 | 120:1 | 0.44 | 73.3 | 5.62 | 0.75 | 96.1 |
| 7 | 40:1 | 0.41 | 72.2 | 5.16 | 0.68 | 94.8 |
| Comparative Example 1 | 25:1 | 1.44 | 10.6 | 2.66 | 0.50 | 14.1 |

Table 2 clearly shows that the comparative absorbing material comprising the H-ZSM-5 type zeolite is useless for selectively isolating the m-dichlorobenzene isomer from other isomers.

EXAMPLES 8 TO 10

In each of Examples 8 to 10, the same procedures as those described in Example 1 were carried out except that the cation H$^+$ in the H-TPZ-3 type zeolite was replaced by Li$^+$ in Example 8, by Na$^+$ in Example 9, and by K$^+$ in Example 10.

The results of the absorption and desorption procedures are shown in Table 3.

TABLE 3

| Example No. | Type of cation in zeolite | Absorption procedure | | | Desorption procedure | |
|---|---|---|---|---|---|---|
| | | Integrated amount of effluent (g) | Average concentration of m-isomer in effluent (% by wt) | m-isomer isolating capacity (C) (% by wt) | Total amount of desorption product (g) | Concentration of p-isomer (% by wt) |
| 8 | Li$^+$ | 0.44 | 79.8 | 6.12 | 0.77 | 98.1 |
| 9 | Na$^+$ | 0.43 | 78.9 | 5.91 | 0.79 | 96.1 |
| 10 | K$^+$ | 0.40 | 71.6 | 5.00 | 0.78 | 90.4 |

EXAMPLES 11 to 14

In each of Examples 11 to 14, the same procedures as those described in Example 1 were carried out except that the feed had the composition indicated in Table 4.

The results of the absorption and adsorption procedures are shown in Table 4.

TABLE 4

| Example No. | Composition of feed | | | Absorption procedure | | | Desorption procedure | |
|---|---|---|---|---|---|---|---|---|
| | o-isomer (% by wt) | p-isomer (% by wt) | m-isomer (% by wt) | Integrated amount of effluent (g) | Average concentration of m-isomer in effluent (% by wt) | m-isomer isolating capacity (C) (% by wt) | Total amount of desorption product (g) | Total Concentration of o- and p-isomers (% by wt) |
| 11 | — | 15.0 | 85.0 | 2.46 | 94.9 | 40.7 | 0.34 | 85.8 |
| 12 | 70.0 | — | 30.0 | 0.43 | 78.1 | 5.85 | 0.74 | 92.3 |
| 13 | 30.0 | — | 70.0 | 1.40 | 90.3 | 22.0 | 0.52 | 84.2 |
| 14 | 46.0 | 24.0 | 30.0 | 0.44 | 74.0 | 5.67 | 0.69 | 92.1 |

In the absorption procedure in Example 14, the breakthrough point occurred about 30 minutes after the start of the absorption procedure.

We claim:

1. A method for a selective isolation of m-dichlorobenzene comprising the steps of:
    bringing an isomeric mixture containing m-dichlorobenzene and at least one member selected from o- and p-dichlorobenzenes into contact with an absorbing material comprising a TPZ-3 type zeolite consisting essentially of at least one aluminosilicate compound of the formula (I):

$$M_{2/n}O \cdot Al_2O_3 \cdot xSiO_2 \cdot mH_2O \qquad (I)$$

wherein M represents a member selected from monovalent and divalent cations, $\underline{n}$ represents an integer of 1 when M represents a monovalent cation, or of 2 when M represents a divalent cation, $\underline{x}$ represents an integer of 10 or more, and $\underline{m}$ represents zero or an integer of 1 or more, to cause the o- and p-dichlorobenzene in the isomeric mixture to be selectively absorbed by the absorbing material; and
    collecting the selectively non-absorbed fraction of the isomeric mixture.

2. The method as claimed in claim 1, wherein in the aluminosilicate compound of the formula (I), the cation represented by M is selected from the group consisting of H$^+$, Na$^+$ and Li$^+$.

3. The method as claimed in claim 1, wherein the aluminosilicate compound of the formula (I) is in anhydride form.

4. The method as claimed in claim 1, wherein contact of the isomeric mixture with the absorbing material is carried out at a temperature of from room temperature to 350° C.

5. The method as claimed in claim 1, wherein the contact of the isomeric mixture with the absorbing material is carried out under a pressure of from ambient atmospheric pressure to about 50 kg/cm$^2$.

6. A method for a selective isolation of m-dichlorobenzene comprising the steps of:

bringing an isomeric mixture containing m-dichlorobenzene and o-dichlorobenzene into contact with an absorbing material comprising a TPZ-3 type zeolite consisting essentially of at least one aluminosilicate compound of the formula (I):

$$M_{2/n}O \cdot Al_2O_3 \cdot \underline{x}SiO_2 \cdot \underline{m}H_2O \qquad (I)$$

wherein M represents a member selected from monovalent and divalent cations, n represents an integer of 1 or more, and M represents a divalent cation, $\underline{x}$ represents an integer of 10 or more, and $\underline{m}$ represents zero or an integer of 1 or more, to cause the o-dichlorobenzene in the isomeric mixture to be selectively absorbed by the absorbing material; and collecting the selectively non-absorbed fraction of the isomeric mixture.

7. The method as claimed in claim 6, wherein in the aluminosilicate compound of the formula (I), the cation represented by M is selected from the group consisting of H+, Na+ and Li+.

8. The method as claimed in claim 6, wherein the aluminosilicate compound of the formula (I) is in anhydride form.

9. The method as claimed in claim 6, wherein contact of the isomeric mixture is carried out at a temperature of from room temperature to 350° C.

10. The method as claimed in claim 6, wherein the contract of the isomeric mixture with the absorbing material is carried out under a pressure of from ambient atmospheric pressure to about 50 kg/cm2.

11. A method for a selective isolation of m-dichlorobenzene comprising the steps of:

bringing an isomeric mixture containing m-dichlorobenzene and p-dichlorobenzene into contact with an absorbing material comprising a TPZ-3 type zeolite consisting essentially of at least one aluminosilicate compound of the formula (I):

$$M_{2/\underline{n}}O \cdot Al_2O_3 \cdot \underline{m}_L H_2O \qquad (I)$$

wherein M represents a member selected from monovalent and divalent cations, $\underline{n}$ represents an integer of 1 when M represents a divalent cation, $\underline{x}$ represents an integer of 10 or more, and $\underline{m}$ represents zero or an integer of 1 or more, to cause the p-dichlorobenzene in the isomeric mixture to be selectively absorbed by the absorbing material; and collecting the selectively non-absorbed fraction of the isomeric mixture.

12. The method as claimed in claim 11, wherein in the aluminosilicate compound of the formula (I), the cation represented by M is selected from the group consisting of H+, Na+ and Li+.

13. The method as claimed in claim 11, wherein the aluminosilicate compound of the formula (I) is in anhydride form.

14. The method as claimed in claim 11, wherein contact of the isomeric mixture is carried out at a temperature of from room.

15. The method as claimed in claim 11, wherein contact of the isomeric mixture is carried out at a temperature of from room temperature to 350° C.

16. The method as claimed in claim 11, wherein the contact of the isomeric mixture with the absorbing material is carried out under a pressure of from ambient atmospheric pressure to about 50 kg/cm2.

* * * * *

UNITED STATES PATENT AND TRADEMARK OFFICE
CERTIFICATE OF CORRECTION

PATENT NO. : 4,873,383
DATED : October 10, 1989
INVENTOR(S) : Toshitaka Kaneshiki et al.

It is certified that error appears in the above—identified patent and that said Letters Patent is hereby corrected as shown below:

Correct the title to read as follows:

--METHOD FOR SELECTIVE ISOLATION OF m-DICHLOROBENZENE-- .

Signed and Sealed this

First Day of January, 1991

Attest:

HARRY F. MANBECK, JR.

*Attesting Officer*  *Commissioner of Patents and Trademarks*